US00PP23018P3

(12) United States Plant Patent
Korlipara

(10) Patent No.: US PP23,018 P3
(45) Date of Patent: Sep. 4, 2012

(54) ***ECHINACEA* PLANT NAMED 'SECRET PASSION'**

(50) Latin Name: ***Echinacea* spp.**
Varietal Denomination: Secret Passion

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 84 days.

(21) Appl. No.: 12/931,231

(22) Filed: Jan. 26, 2011

(65) Prior Publication Data

US 2012/0192324 P1 Jul. 26, 2012

(51) Int. Cl.
*A01H 5/00* (2006.01)

(52) U.S. Cl. ..... Plt./428

(58) Field of Classification Search ..... Plt./428
See application file for complete search history.

*Primary Examiner* — June Hwu

(74) *Attorney, Agent, or Firm* — Klarquist Sparkman, LLP

(57) ABSTRACT

A new and distinct *Echinacea* plant named 'Secret Passion' characterized by enlarged disc florets forming an anemone-type inflorescence, warm pink ray florets contrasting strongly with the deep flamingo pink disc florets, a low habit with good branching, and excellent vigor.

1 Drawing Sheet

Botanical denomination: *Echinacea* spp.

Variety designation: 'Secret Passion'.

The present invention relates to a new and distinct cultivar of *Echinacea* and given the cultivar name 'Secret Passion'. *Echinacea* is in the family Asteraceae. This new cultivar is a third generation seeding originating from a planned breeding program using *Echinacea purpurea* 'Razzmatazz' (U.S. Plant Pat. No. 13,894) as the seed parent in the original cross and unnamed proprietary, unreleased interspecific hybrids for the pollen parent. The exact parents of this selection are unknown, unnamed, proprietary plants.

Compared to *Echinacea purpurea* 'Razzmatazz' (U.S. Plant Pat. No. 13,894), the seed parent in the original breeding line, the new variety is shorter with more crowns, and with larger, darker pink inflorescences.

Compared to *Echinacea* 'Pink Double Delight' (U.S. Plant Pat. No. 18,803), the new cultivar has more crowns, inflorescences with darker pink discs and that have a stronger contrast between the ray and disk florets.

This new *Echinacea* cultivar is distinguished by:

1. enlarged disc florets forming an anemone-type inflorescence,
2. warm pink ray florets contrasting strongly with the deep flamingo pink disc florets,
3. a low habit with good branching, and
4. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the inflorescences of *Echinacea* 'Secret Passion'.

FIG. 2 shows a field row of one-year-old plants in early August in Canby, Oreg.

DETAILED PLANT DESCRIPTION

The following is a detailed description of the new *Echinacea* cultivar based on observations of a 2-year-old specimens growing in the 2-gallon pots outdoors in the nursery in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart, 5$^{th}$ edition.

Plant:

*Type.*—Herbaceous perennial.
*Hardiness.*—USDA Zones 4 to 9.
*Size.*—Grows to about 74 cm wide and 74 cm tall to top of inflorescences.
*Form.*—Basal clump, with about 30 stems from the base.
*Vigor.*—Excellent.
*Roots.*—Fibrous, with many downward growing and few laterals, ivory in color, Yellow White 158D, roots develop easily from cuttings from the crown.

Stem (flowering):

*Type.*—Ascending, with 1 to 2 inflorescences per stem.
*Size.*—To 72 cm tall to a terminal inflorescence and 5 mm wide at base.
*Internode length.*—5 cm to 12 cm.
*Surface texture.*—Strigose.
*Color.*—Yellow Green 144A mottled Greyed Purple N186A and tinted in sun with Greyed Purple N186C.

Leaf (basal):

*Type.*—Simple.
*Shape.*—Lanceolate.
*Arrangement.*—Basal.
*Blade size.*—Grows to 11 cm long and 3 cm wide.
*Margins.*—Sparsely serrate.
*Apex.*—Acute.
*Base.*—Attenuate.

*Surface texture.*—Strigose on both sides.

*Venation.*—Pinnate, with 3 main veins.

*Color.*—Topside, Green N137C, bottom side Yellow Green 147B.

*Petiole description.*—Grows to 12.5 cm long and 1.4 mm wide, glabrous, Yellow Green 146B.

Leaf (stem):

*Type.*—Simple.

*Shape.*—Lanceolate.

*Arrangement.*—Alternate.

*Blade size.*—Grows to 12 cm long and 3.5 cm wide.

*Margins.*—Entire to sparsely serrate.

*Apex.*—Acuminate.

*Base.*—Attenuate.

*Surface texture.*—Strigose on both sides.

*Venation.*—Pinnate, with 3 main veins from the base.

*Color.*—Topside, Green 137A, bottom side closest to Yellow Green 147B.

*Petiole description.*—On lowermost leaves only, clasping, grows to 10 cm long and 2 mm wide above the clasp, glabrous, Yellow Green 146C.

Inflorescence:

*Type.*—Composite on terminal stalked heads.

*Number of flowering stems per plant.*—About 30.

*Flowering stem.*—Grows to 72 cm tall from the base of the plant to the terminal inflorescence and can grow to 24 cm long from the top stem leaf to the base of an inflorescence; branched, with 1 to 2 inflorescences per stem; diameter growing to 8 mm wide near the inflorescence; strigose; Yellow Green 144A mottled Greyed Purple N186A.

*Size.*—Grows to 10 cm wide and 6 cm deep as disc enlarges.

*Form.*—Ray florets held slightly reflexed, mature disc is conic.

*Immature inflorescence.*—Grows to 3 cm wide and 2.2 cm deep, ray florets held upright and rolled up so only the back color shows, Yellow 11C with Green Yellow 1A on tip and tinted Red Purple 63A in the middle, disc color Yellow Green 146B.

*Ray florets.*—Without pistil or stamen, about 20 in number, grow to 55 mm long and 10 mm wide, oblanceolate with the tip two toothed (each acute), entire margins, base attenuate, glabrous on both sides; topside Red 55B, bottom side closest to Greyed Purple 185D.

*Disc.*—Flat becoming conic, becoming 30 mm deep and 70 mm wide with maturity, overall color is Red 53D.

*Disc florets.*—About 250 in number, each with 1 pistil and 4 stamen, grow to 32 mm long and 8 mm wide, each with one persistent, very stiff linear bract (14 mm long with the top 2 mm colored Red 45A on tip then Yellow Green 144A in middle, then White NN155D on bottom ⅓); showy 4 to 5 lobed corollas to 24 mm long and 8 mm wide, tubular on the bottom with the lobes spread out like a fan, glabrous on both sides, topside color Red 46B, back side color Greyed Purple 185C; pistil 9 mm long, ovary 2.5 mm long, White NN155D, style 3 to 5 mm long White 155A, 2-branched stigma spreading, Greyed Purple 187A; stamen 4 mm long, anthers 1.5 mm long and Greyed Purple N186A, filaments 2.5 mm long, White 155A, very little pollen, Yellow Orange 23B.

*Phyllaries.*—In 4 leafy series, area 3 cm wide and 8 mm deep, lobes lanceolate in shape, reflexed, grow to 15 mm long and 4 mm wide, Yellow Green 147B, margins strigose, tip acute, strigose on both sides.

*Receptacle.*—Grows to 12 mm wide and 15 mm deep, White 155A.

*Bloom period.*—July through October in Canby, Oreg.

*Fragrance.*—Good, floral.

*Lastingness.*—Each inflorescence lasts about two weeks in Canby, Oreg.

Seeds: 0 to 1 per inflorescence, each 3 mm long and 2.5 mm wide, oval, Brown 200C.

*Fertility.*—Poor.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

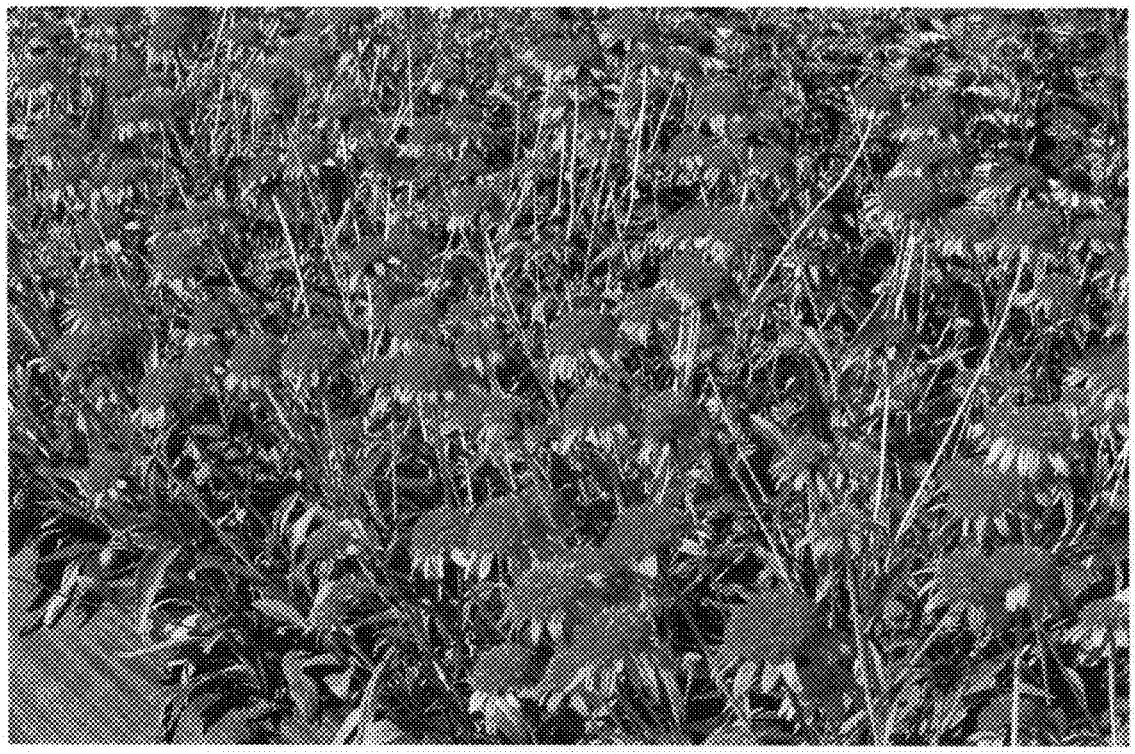

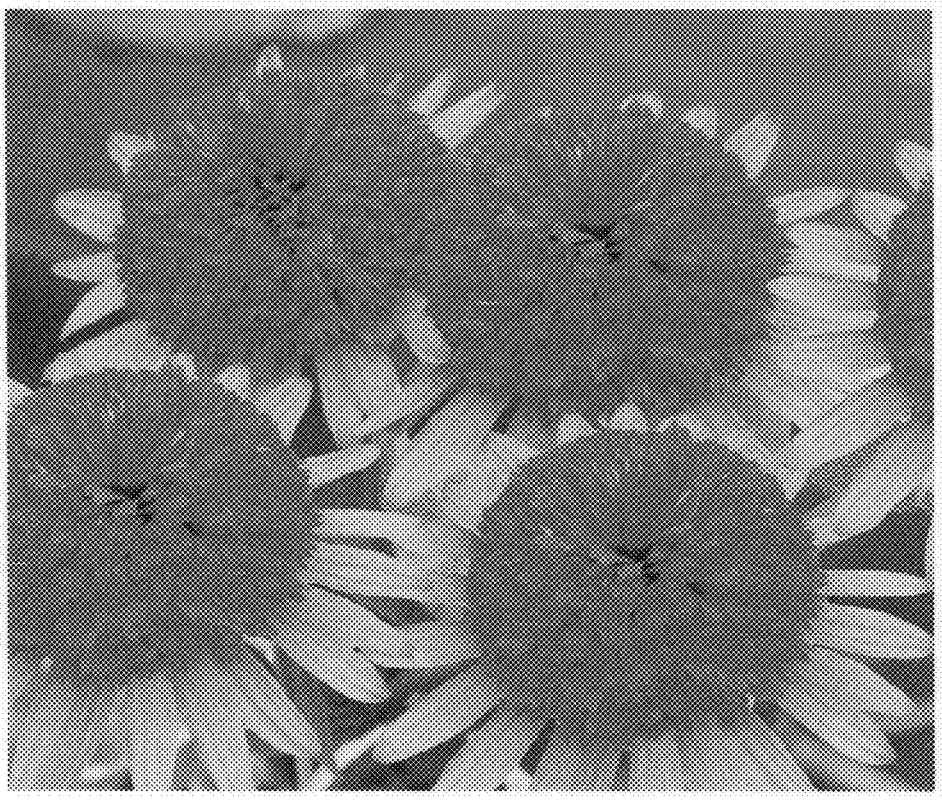
Figure 1 above
Figure 2 below